United States Patent
Brown et al.

(10) Patent No.: US 9,615,943 B2
(45) Date of Patent: Apr. 11, 2017

(54) ADJUSTABLE MODULAR PROSTHESIS

(71) Applicant: Biomet Manufacturing, LLC, Warsaw, IN (US)

(72) Inventors: David R. Brown, Warsaw, IN (US); Aaron P. Smith, Warsaw, IN (US); Trent Bauters, Akron, IN (US); Kirk J. Bailey, Rochester, IN (US); John R. White, Winona Lake, IN (US); Tony Siebeneck, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 14/642,094

(22) Filed: Mar. 9, 2015

(65) Prior Publication Data

US 2015/0250620 A1 Sep. 10, 2015

Related U.S. Application Data (60) Provisional application No. 61/950,401, filed on Mar. 10, 2014.

(51) Int. Cl.
| | | |
|---|---|---|
| *A61F 2/38* | (2006.01) | |
| *A61F 2/46* | (2006.01) | |
| *A61F 2/30* | (2006.01) | |
| *A61F 2/36* | (2006.01) | |

(52) U.S. Cl.
CPC ............ *A61F 2/4684* (2013.01); *A61F 2/389* (2013.01); *A61F 2002/3055* (2013.01); *A61F 2002/365* (2013.01); *A61F 2002/3625* (2013.01)

(58) Field of Classification Search
CPC ...... A61F 2/34; A61F 2/36; A61F 2/38; A61F 220/0025; A61F 2/389; A61F 2/4684; A61B 17/1739; A61B 17/1742
See application file for complete search history.

(56) References Cited

U.S. PATENT DOCUMENTS

| | | | | |
|---|---|---|---|---|
| 5,569,263 A | * | 10/1996 | Hein ..................... | A61F 2/4684 606/102 |
| 5,800,556 A | * | 9/1998 | Sanders ................ | A61F 2/4684 606/102 |
| 5,888,211 A | * | 3/1999 | Sanders ................ | A61F 2/4684 606/102 |

* cited by examiner

*Primary Examiner* — Jason-Dennis Stewart
(74) *Attorney, Agent, or Firm* — Schwegman Lundberg & Woessner, P.A.

(57) ABSTRACT

Disclosed is a modular trial system to select a neck length. The system may be in a hexagonal or click embodiments. A neck member may having at least a locating step with a locating step face. A head member may have at least a first groove and a second groove in an internal bore. The head member may be rotated relative to the neck member to select various trial lengths of the neck.

20 Claims, 8 Drawing Sheets

ADJUSTABLE MODULAR PROSTHESIS

CROSS-REFERENCE TO RELATED APPLICATIONS

This application claims the benefit of U.S. Provisional Application No. 61/950,401, filed on Mar. 10, 2014. The entire disclosure(s) of (each of) the above application(s) is (are) incorporated herein by reference.

FIELD

The present disclosure relates to an adjustable modular prosthesis trialing method and apparatus.

BACKGROUND

This section provides background information related to the present disclosure which is not necessarily prior art.

When performing a procedure on a patient, a prosthesis can be used to replace or augment a natural anatomical feature. For example, due to age, injury, disease, or other causes, a portion of the anatomy may need to be replaced or resurfaced. Examples include replacing an acetabulum on a patient either in conjunction with or separate from replacing or resurfacing a femoral head. An acetabular prosthesis is generally positioned within a prepared acetabulum.

Positioning an acetabular prosthesis or tibial bearing relative to another prosthetic portion can include various dexterous movements. The acetabular prosthesis or tibial bearing is generally positioned with a selected alignment and position relative to a tibial bone. The alignment of the acetabular prosthesis or tibial bearing can include rotational positioning that is generally selected relative to the natural anatomy. The prosthesis includes a central axis that is aligned and positioned at a certain depth that is selected to be aligned and positioned with a portion of the natural anatomy. In positioning the acetabular prosthesis or tibial bearing in the selected position, both position and axial alignment can be selected. Each patient may require a different alignment and axial position that is generally unknown prior to the procedure. Positioning the acetabular prosthesis or tibial bearing requires the user, such as a surgeon, to position the acetabular prosthesis or tibial bearing appropriately in a patient's anatomy. The correct position may require the user to use a trial-and-error method, where several prostheses of different sizes are positioned in the patient's anatomy, measured, and removed during a trial procedure. Accordingly, the trial-and-error process is time consuming.

SUMMARY

This section provides a general summary of the disclosure, and is not a comprehensive disclosure of its full scope or all of its features.

Herein disclosed is a modular trial system to select a neck length. The system may select the length using various configurations or embodiments, such as a hexagonal configuration or a click configuration. In both embodiments a neck member may have at least a locating step with locating step face. The locating step face is formed by a flat surface at an angle, such as perpendicular, to a central axis of the neck member. The system also includes a head member having an internal bore with a first end and a second end. The head member may have at least a first groove and a second groove in the internal bore. A first step face of a first step is nearer the second end than a second step face of a second step. In addition, the locating step face is configured to selectively engage the first step face or the second step face to select a first neck length or a second neck length. In various embodiments, the head member is selectively and discretely rotatable relative to the neck member. In various embodiments, a first member with a step face can engage a slot or groove in a second member such as by deflecting into the groove.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

An adjustable modular prosthesis for trialing may include various portions for connection between two prosthetic members or at least one natural anatomical member. For example, in a proximal femoral prosthesis a trial system may include a head member, a neck member and various members to be positioned in a bone portion for trialing.

A Hexagonal Shaped Embodiment

Figure 1:
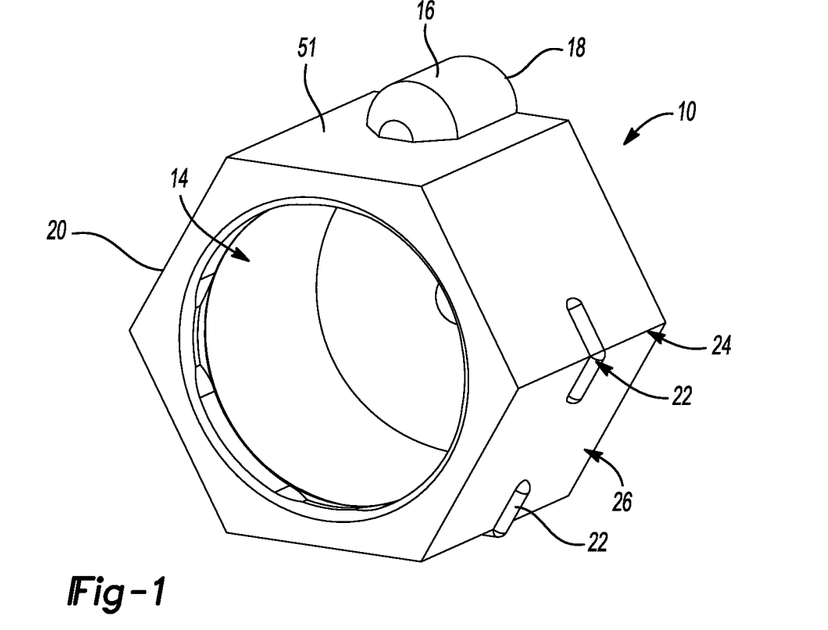
FIG. 1 is a perspective view of a hexagonal neck member.
Figure 2:
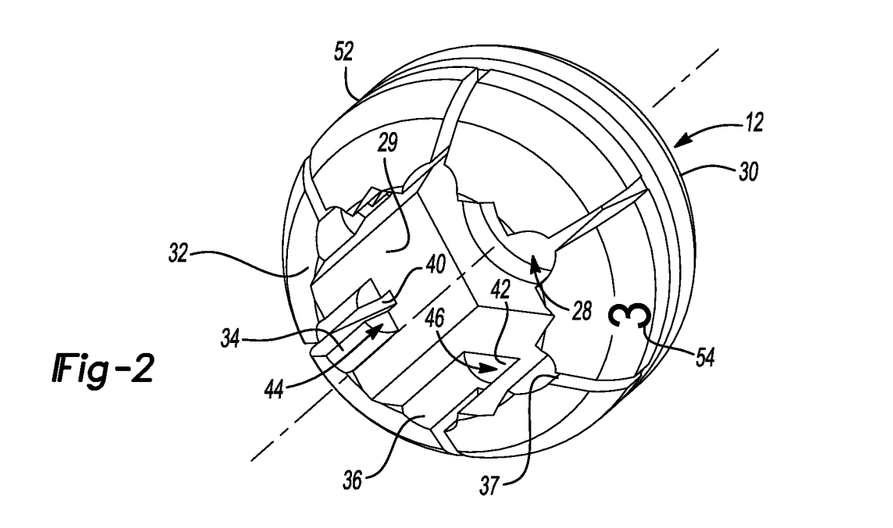
FIG. 2 is a perspective view of a hexagonal head member.
Figure 3:
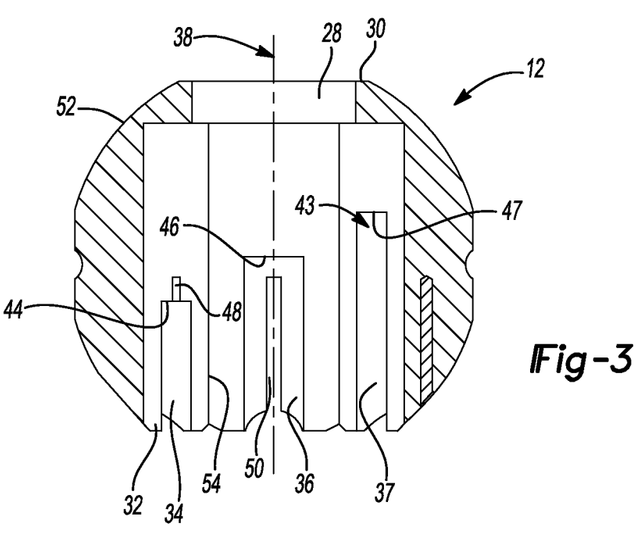
FIG. 3 is a cross-sectional view of the hexagonal head member.
Figures 6, 7:
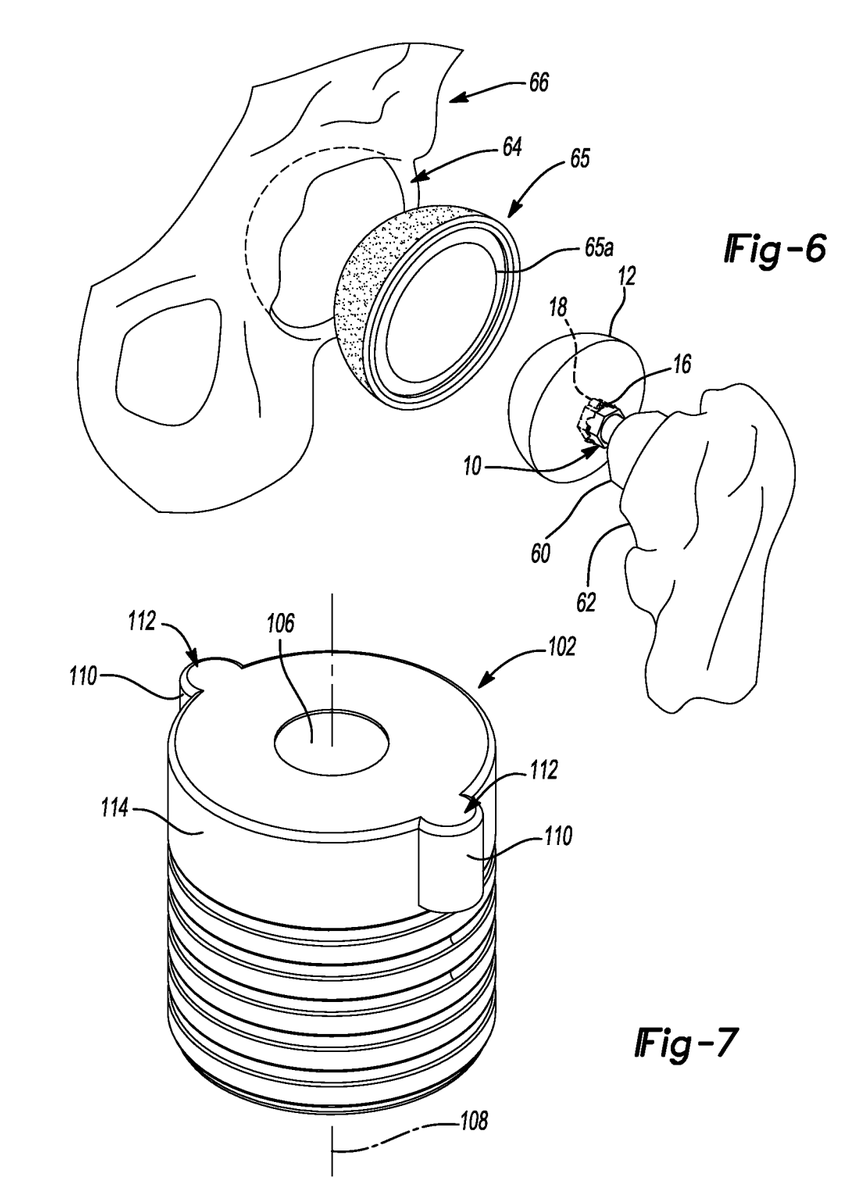
FIG. 6 is an environmental view of a trial femoral prosthesis.
FIG. 7 is a perspective view of a circular neck member.

A hexagonal embodiment, as illustrated in FIGS. 1-3, may include at least a two member system. The system may include at least a neck member 10 and a head member 12. The system is generally made of a biocompatible material, such as biocompatible metals and/or polymers, or combinations thereof, although a person of skill in the art could make the system from many materials. The head member 12 is selectively and discretely rotatable relative to the neck member 10 by a plurality of grooves, as described below. The neck member 10 is generally sized to fit within the head member 12. The neck member 10 has a generally hexagonal cross-section, although other cross-sections, such as circular, could be used (FIG. 7). The cross-section shape, it is understood, may be any appropriate shape and may be determined by the number of length variations. The neck member 10 may also include a central bore 14 about a central longitudinal axis. The neck member 10 may also comprise an X-Ray marker (not shown) to make the member 10 visible or opaque to an X-Ray imaging system.

The neck member 10 may also comprise at least one locating step 16 with a locating step face 18. The locating step 16 is generally positioned around a perimeter 20 of the neck member 10. The locating step 16 may be a projection from the neck member 10 and extend from a wall or face surface 26 forming the perimeter 20 of the neck member 10. The locating step face 18 may be a generally flat surface on the locating step 16 and extend at an angle, such as generally perpendicular, to a central axis of the neck member 10. There may be only one locating step 16 or the neck member 10 may have numerous locating steps 16 positioned at different locations around the neck member 10 (e.g. FIG. 7). If the neck member 10 has many locating steps 16, they may generally be spaced evenly around the perimeter 20 of the neck member 10. For example, if the neck member 10 has two locating steps 16, each locating step 16 may be positioned on opposing sides of the neck member 10. More locating steps 16 may be preferred to only one step 16, as described below, for example, to improve the system's stability and distribute engagement forces. The locating step 16 may be formed in many shapes. In the illustrated embodiment, although, the step 16 is generally curved or partially cylindrical.

The neck member 10 may also include at least one or more than one locking features 22. The locking features 22 are located on the perimeter 20 of the neck member 10. For example, the locking features 22 may be specifically located on an edge 24 of the hexagonal neck member 10. Alternatively, the locking features 22 may be located on the hexagonal neck member faces 26. The locking features 22 engage with an internal bore 28 of the head member 12 when the user inserts the neck member 10 into the head member 12 to restrict movement of the neck member 10 axially and/or circumferentially by providing additional friction. The locking features 22 are generally fixed linear protrusions, although a skilled person in the art will understand many other shapes that restrict movement, such as non-linear notches or detachable steps (not shown). It is understood, also, that the steps and engaging features may be reversed or placed on the opposed pieces.

Figure 8:
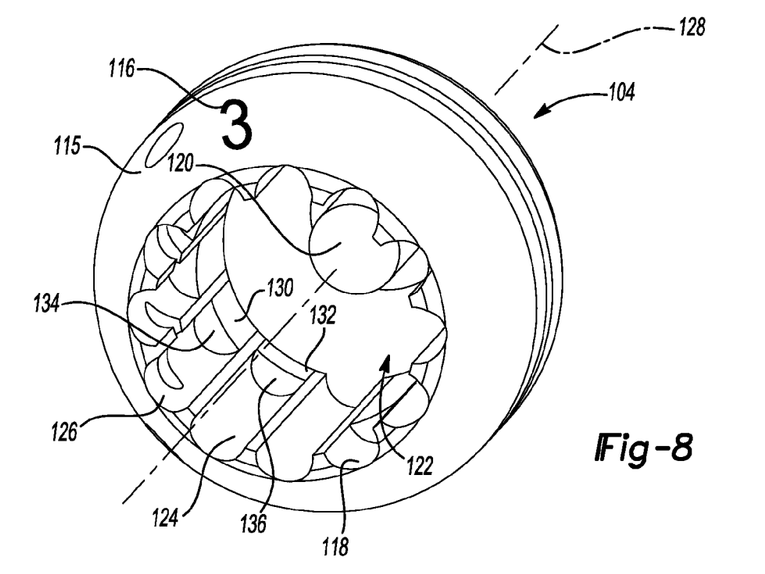
FIG. 8 is a perspective view of a circular head member.

The head member 12 may be a femoral head member to be positioned in an acetabulum during prosthesis trialing. The head member 12 may have the internal bore 28 that extends from a first end 30 to a second end 32. The internal bore may have a hexagonal cross-section, although other cross-sections, such as circular, could be used (FIG. 8). The internal bore 28 is formed by one or more walls 29. Formed in at least one of the walls 29 is a locating groove, which may include three separate locating grooves 34, 36, and 37. Any appropriate number of locating grooves may be formed. With reference to FIGS. 2 and 3, the locating grooves 34-37 may extend generally parallel to a longitudinal axis 38 of the internal bore 28. Furthermore, the grooves 34-37 may extend through the second end 32, but need not extend through the first end 30. Although it is understood that each of the grooves 34-37 may include similar features, discussion herein, for clarity, is directed to the first groove 34 and the second groove 36.

The first groove 34 includes a first step 40, the second groove 36 includes a second step 42, and the third groove 37 includes a third step 43. The first step 40, the second step 42, and the third step 43 include a first step face 44, a second step face 46, and a third step face 47, respectively. The first step face 44 of the first step 40 is nearer the second end 32 than the second step face 46 of the second step 42. As discussed below, the locating step 16 can be inserted into at least one of the selected grooves 34-37 and engage at least one of the faces 44-47.

The head member 12 may also include a first sliding groove 48 that can cooperate and/or extend from the first groove 34 and a second sliding groove 50 that can cooperate with the second groove 36. Generally, the first groove 34 is parallel to the first sliding groove 48 and the second groove 36 is parallel to the second sliding groove 50. The sliding grooves 48, 50 may extend through the head member 12. The sliding grooves 48, 50 may provide stress relief for insertion of the neck member 10. Further, the internal bore 28 of the head member 12 may include corners 51 that may slidably engage with the hexagonal corners of the neck member 12 to allow the locating step 16 to engage with at least one of the locating grooves 34, 36, 37 of the head member 12.

An exterior 52 of the head member 12 may have markings 54 near the grooves 34, 36, 37 at or near the second end 30. The markings 54 may correspond to a trial length of the groove adjacent to the grooves 34-37. For example, a "6" marking 54 may indicate that a proximate groove has a trial length of 6 mm. The markings may have different sizes, fonts, colors, or even engravings to be readable to the user.

Figure 4:
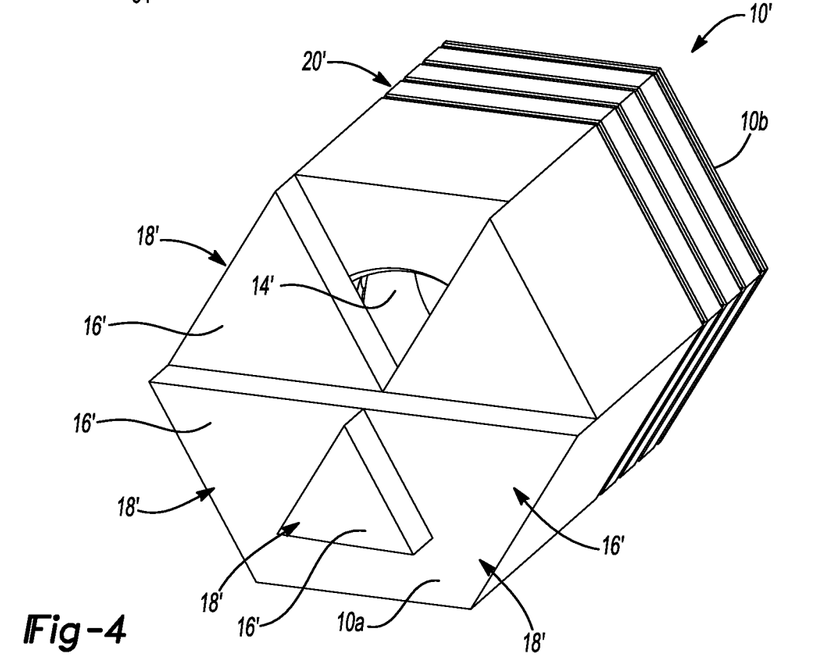
FIG. 4 is a perspective view of a hexagonal neck member.
Figure 5:
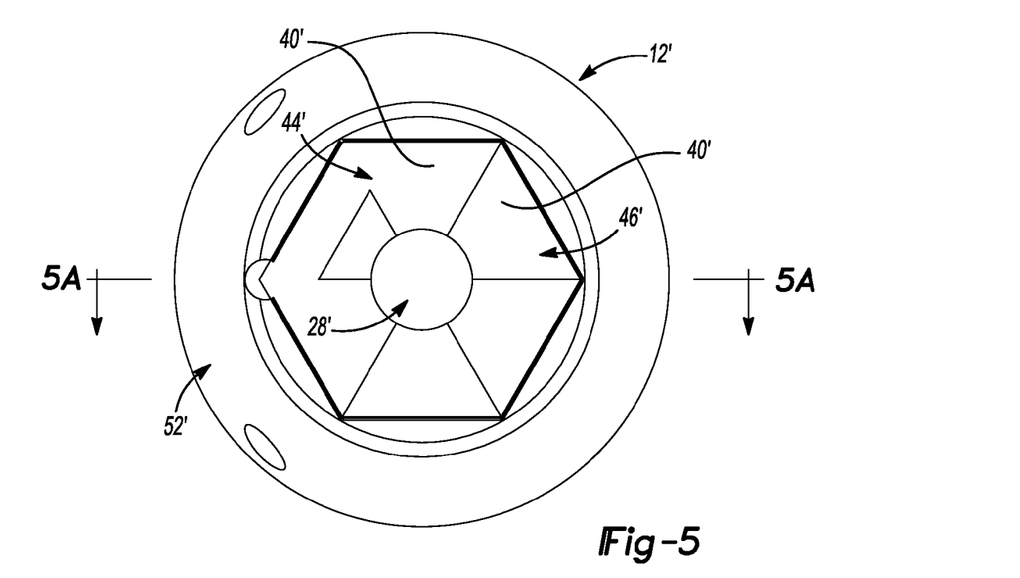
FIG. 5 is a top view of a hexagonal head member.
Figure 5A:
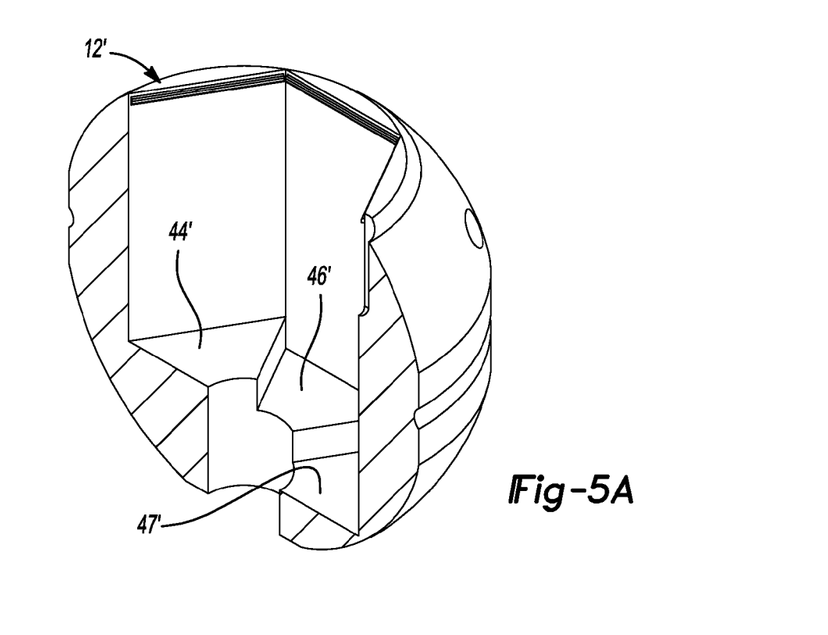
FIG. 5A is a cross-sectional view of the hexagonal head member.

FIGS. 4-5A shows an alternative embodiment of the hexagonal embodiment, where similar features to those discussed related to the embodiment illustrated in FIGS. 1-3 are augments with a prime. A hexagonal neck member 10' may have multiple locating steps 16'. Each of the locating steps 16' may have a locating step face 18', which may have a trapezoidal-like shape. The locating step faces 18' will be arranged at different distances relative to a first end 10a and a second end 10b of the neck member 10'. Each locating step 16' is arranged in a staircase-like pattern around a central bore 14' of the neck member 10', rather than on a perimeter 20' of the neck member 10'. There may be two staircase-like patterns on opposing sides of the neck member 10', such that more than one locating face 18' is at the same distance relative to the first end 10a and second end 10b.

Furthermore, the head member 12', as shown in FIGS. 5 and 5A, has first groove step face 44', second groove step face 46', and third groove step face 47', arranged in a staircase-like pattern around the internal bore 28'. More than one locating step face 18' may engage with at least one of the groove step faces 44'-47' of the head member. If more than one locating step face 18' engages with more than one of the groove step faces 44'-47', then each locating step face 18' engages the respective groove step faces 44'-47' with the same force.

Operating the Hexagonal Shaped Embodiment

According to various embodiments, including that illustrated in FIGS. 1-3, a user, such as a surgeon, may position the neck member 10 over a stem 60, as illustrated in FIG. 6, which may be placed in a femur 62. The central bore 14 of the neck member 10 engages with the stem 60. The user may then engage the neck member 10 with the head member 12 by aligning the locating step 16 of the neck member 10 with at least one of the grooves 44-47 of the head member 12 corresponding to a selected trial length, such as shown by the markings 54, then sliding the neck member 10 into the groove of the head member 12. A person skilled in the art will appreciate that methods of engaging, besides sliding, such as rolling or clicking, may be used.

The neck member 10 may stop movement into the head member 12 when the locating step face 18 of the neck member 10 engages the step face 18 of the selected groove, thereby arriving at the selected neck length. The locking feature 22 may assist in maintaining the head 12 at the selected position on the neck member 10. Once positioned in the trial length position, the user may then position the assembly in the patient's acetabulum 64 or in a prosthetic acetabular cup 65 in the patient's pelvis 66. The acetabular cup 65 may include a liner or bearing 65a. Generally, the acetabular cup 65 may be positioned in the acetabulum 64 prior to trialing. Further, the acetabular cup 65 may be a trial cup. The user then moves the stem 60 through a selected range of motion. One skilled in the art should appreciate that the system is suitable outside of a patient's hip, such as use during external trialing or in a shoulder.

Next, the user determines if the selected length is appropriate for the patient. This can be based on, for example, whether the trial range of motion is appropriate and/or consistent with a selected patent plan. If the length is not appropriate, the user may then adjust the length of the neck member 10. As discussed above, the head 12 may be removed from the neck member 10 and the head member 12 may be rotated relative to the neck member 10 to allow engaging of another groove The stem 60 and/or the neck member 10 may remain in place which the used removes and adjusts the head member 12.

A Clock Configuration Embodiment

A clock, cylindrical, or round configuration, illustrated in FIGS. 7 and 8, may include a two member system. The system has a neck member 102 and a head member 104 and an anti-rotation system. The clock configuration is generally made of a biocompatible material, similar to those discussed above, although a person of skill in the art could make the configuration from many materials. The neck member 102 has a generally circular cross-section, although other the neck member 102 could have various cross-sections. The neck member 102 is generally sized to fit within the head member 104. The neck member 102 may also include a central bore 106 about a central longitudinal axis 108. The neck member 102 may also include an X-Ray marker (not shown) to make the neck member 102 visible or opaque to an X-Ray camera.

The neck member 102 may also include at least one locating step 110 with a locating step face 112. Although, as illustrated, more than one of the locating steps 110 may be present with a respective step face 112. The locating step 110 is generally positioned on an exterior surface 114 or around a perimeter of the neck member 102. The neck member 102 may only have one locating step 110 or numerous locating steps 110. If there are many locating steps 110, they are generally spaced evenly around the outer perimeter 114 of the neck member 102. More locating steps 110 may be preferred to only one step 110, as described below. The locating step 110 may be many shapes although the step 110 is generally curved.

The head member 104, in the illustrated embodiment, may be a femoral head, intended to be positioned in the acetabulum during replacement trialing, such as the acetabulum illustrated in FIG. 6. It is understood, however, as discussed above, that the clock configuration may be used for trialing other portions. The head member 104 may form an internal bore 122 with a first end 118 and a second end 120. The internal bore 122 may have a plurality of grooves.

Each of the grooves may have different ends or faces. For the clarity of the current discussion, a first groove 124 and a second groove 126 are specifically described. Other grooves may have similar features with varying depths, similar to the grooves discussed above.

The first groove 124 and the second groove 126 are generally parallel to a longitudinal axis 128 of the internal bore 122. At least the first end 118 of the head member 104 allows the head member 104 to be placed on the neck member 102. The first groove 124 includes a first step 130 and the second groove 126 includes a second step 132. The first and second steps 130, 132 include a first and second step face 134, 136, wherein the first step face 134 is nearer the second end 134 than a second step face 134 of the second step 132. An exterior 115 of the head member 104 has markings 116 proximate to the second end 120 that indicate where the user inserts the neck member 102 and or a length. For example, the exterior 115 of the head member 104 may have markings 116 that indicate "3", which can refer to a 3 millimeter (mm) neck length. It is understood, however, that any appropriate markings may be provided to refer to any appropriate length for the trial system. The markings 116 are positioned on the exterior 115 of the head member 104 such that a user can read them when the neck member 102 is inserted in the head member 104. A skilled person in the art could appreciate that text, symbols, pictures, or other indicia could be used.

Operating the Clock Configuration Embodiment

A user, generally a surgeon, will position the neck member 102 over a stem (similar to FIG. 6). The central bore 106 of the neck member 102 engages with the femoral replacement part. The user then engages the neck member 102 with the head member 104 by sliding the neck member 102 into at least one of the grooves 124, 126 of the head member 104. A selected neck length is achieved by, aligning the locating step 110 of the neck member 102 with one of the selected grooves 124, 126 of the head member 104 corresponding to the desired depth, as shown by the markings 116.

A person skilled in the art would appreciate that methods of engaging, besides sliding, such as rolling or clicking may be used. The may user stop pushing the neck member 102 when the locating step face 112 of the neck member 102 engages the step face 134, 136 of the selected groove, thereby arriving at the selected neck length. The user then positions the head member 104 in the patient's acetabular cup. One skilled in the art should appreciate that the clock design is suitable outside of a patient's acetabular cup, such as during external trialing or in a shoulder.

Next, the user determines if the engaged configuration is appropriate for the patient, for example, whether the range of motion is appropriate and/or consistent with a selected patient plan. If the position is incorrect, the user may then adjust the depth of the neck member 102 within the head member 104 by removing the neck member 102 from the groove 124, 126 and rotating the neck member 102 to another groove corresponding to a different length, which may be marked by the marking 116. The head member 104 may remain in position within the acetabulum of the patient while the user adjusts the neck member 102.

A Click Configuration Embodiment

Figure 9:
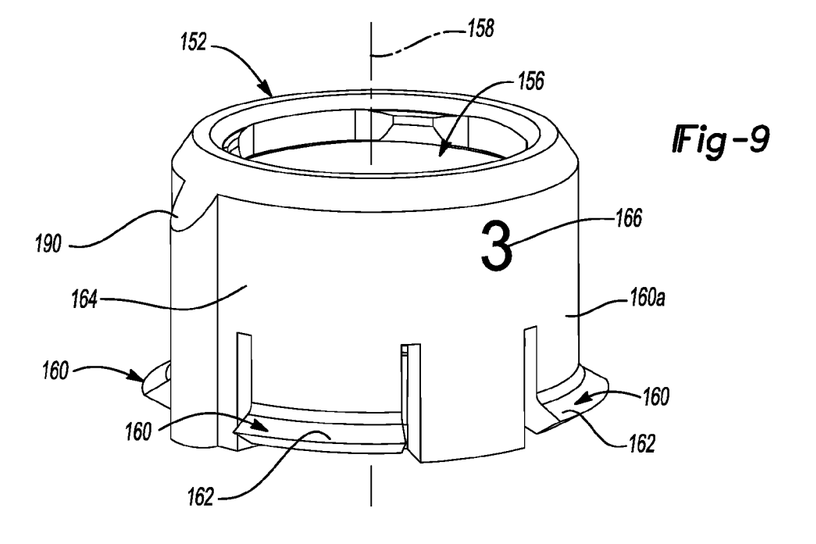
FIG. 9 is a perspective view of a click neck member.
Figure 10A:
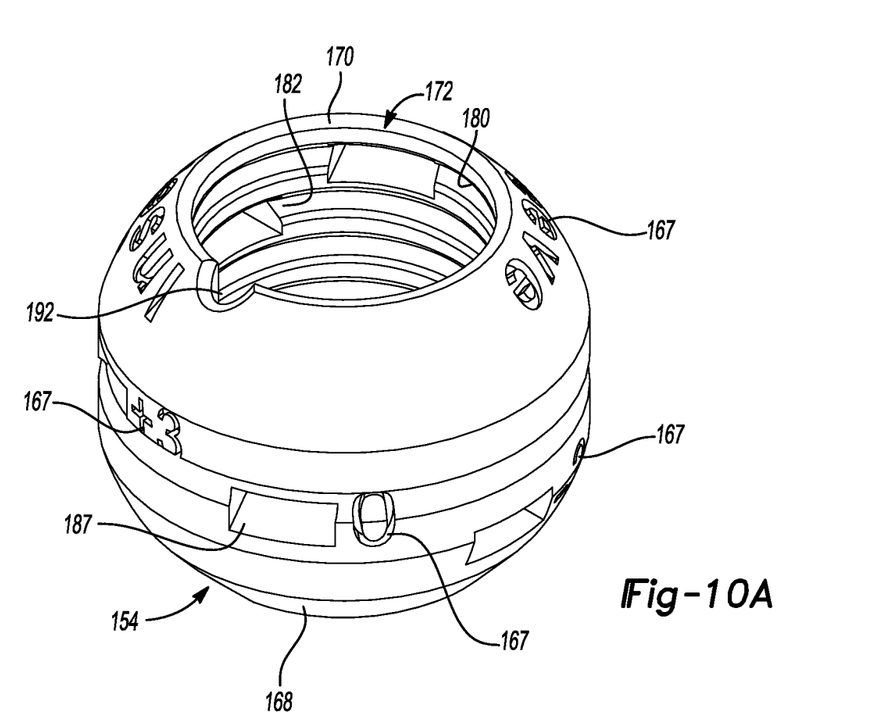
FIG. 10A is a perspective view of a click head member.
Figure 10B:
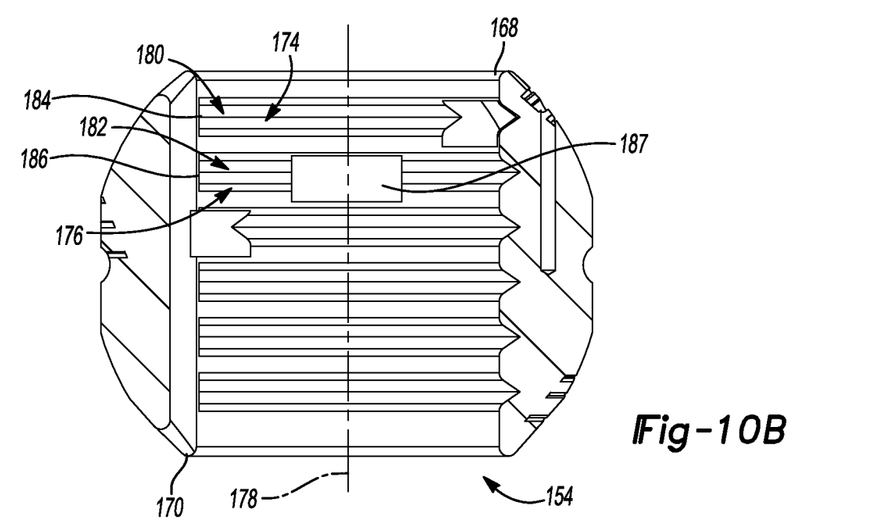
FIG. 10B is a cross-sectional view of the click head member.

A click configuration, illustrated in FIGS. 9-10B, may include a two member system. The system has a neck member 152 and a head member 154 and an anti-rotation system. The click configuration is generally made of a biocompatible material, similar to those discussed above, although a person of skill in the art could make the configuration from many materials. The neck member 152 has a generally circular cross-section, although the neck member 152 could have various cross-sections. The neck member 152 is generally sized to fit within the head member 154. The neck member 152 may also include a central bore 156 about a central longitudinal axis 158. The neck member 152 may also include an X-Ray marker (not shown) to make the neck member 152 visible or opaque to an X-Ray camera, is the neck member 152 is formed of a non-opaque material.

The neck member 152 may also include at least one locating step 160 with a locating step face 162. Although, as illustrated, more than one of the locating steps 160 may be present, and each step may have a respective step face 162. The locating step 160 may be formed on or extend from an exterior surface 164 of the neck member 152. If there are many locating steps 160, they are generally spaced evenly around the exterior surface 164 of the neck member 152. If more than one of the locating steps 160 is provided, as illustrated, each step 160 may engage the head member 154 as discussed herein. This may evenly distribute a force among the various steps 160. The locating step 160 may be many shapes although the step 160 is generally curved.

The exterior surface 164 of the neck member 152 may have markings 166. The markings 166 may correspond to a length when the neck member 152 is inserted in the head member 154 up to the marking 166 proximate to the first end 168 of the head member 154. For example, when a "3" marking is visible proximate to the first end 168 of the head member 154, the device may indicate that the locating step 160 is at a length of 3 millimeters (mm). The markings 166 may have different sizes, fonts, colors, or even engravings to be readable to the user. As discussed herein, markings 167 may also be presented on the head member 154.

The head member 154, in the illustrated embodiment in FIGS. 10A and 10B, may be a femoral head, intended to be positioned in the acetabulum during replacement trialing, such as the acetabulum illustrated in FIG. 6. It is understood, however, as discussed above, that the click configuration may be used for trialing other portions, such as other anatomical portions of a human patient. The head member 154 may form an internal bore 172 with a first end 168 and a second end 170. The internal bore 172 may have a plurality of grooves 174, 176. Each of the grooves 174, 176 are generally formed as annular grooves in a wall of the head 154 that forms the bore 172. Each of the grooves may have different surfaces or faces to engage the locating step 160, as discussed herein. For the clarity of the current discussion, a first groove 174 and a second groove 176 are specifically described.

The first groove 174 and the second groove 176 are generally annularly formed around a longitudinal axis 178 of the internal bore 172. At least the first end 168 of the head member 154 allows the head member 154 to be placed on the neck member 152. The first groove 174 includes a first step 180 and the second groove 176 includes a second step 182. The first step 180 and the second step 182 include a first step face 184 and a second step face 186, respectively, wherein the first step face 184 is nearer the second end 170 than a second step face 186 of the second step 182.

Formed through the head member 154 may be one or more openings 187. The openings 187 may be adjacent to the markings 167 on the exterior 165 of the head 154. Viewed through the openings 187 may be a marking or indication on the neck 152. The neck indication may be the marking 166 or other appropriate marking or portion, such as a projection. If the marking on the neck 152 is viewable through one of the openings 187, the head marking 167 may be read as the length of the trial. For example, if the neck marking is viewed through the opening 187 near the marking "+3" the user can be notified that the trial is set at 3 mm. Further, the markings 167 can indicate which end of the head 154 that the neck member 152 should be first positioned.

The click configuration may also include an anti-rotation system. The anti-rotation system may restrict the neck member 152 and the head member 154 from rotating relative to one another when the neck member 152 is coupled to the head member 154. The anti-rotation system may include a key 190 on the exterior surface 164 of the neck member 152. If the neck member 152 has more than one locating step 180, the key 190 is positioned between two locating steps 180, 182. The key 190 may also have a semi-circular or rectangular cross-section. A key groove 192 has a generally complimentary cross-section to the key 190 of the neck member 152, although a skilled person in the art would appreciate that the key groove 192 and the key 190 may have a non-complimentary cross-section. The key groove 192 may extend at least a portion of the length of the internal bore 172 and may be parallel to the longitudinal axis 178 of the internal bore 172. The key groove 192 may extend through the second end 170, however, the key groove 192 does not extend through the first end 168. The key groove 192 is adapted to slidably couple with a key 190 on the neck member 152, as described below.

Operating the Click Configuration Embodiment

A user, generally a surgeon, will position the neck member 152 over a stem (similar to FIG. 6). The central bore 156 of the neck member 152 engages with the femoral replacement part. The user then engages the neck member 152 with the head member 154 by sliding the neck member 152 and the locating step 160 into at least one of the grooves (e.g. grooves 174, 176) of the head member 154. A selected neck length is achieved by aligning the locating step 180 of the neck member 152 with one of the selected grooves 174, 176 of the head member 154 corresponding to the desired depth, as shown by the markings 166, 167. The user may press or pinch the locating steps 180, 182 to couple the neck member 152 with the head member 154. It is understood, however, that an axial force may cause the locating steps 160 or a finger 160a from which the locating step 160 extends, to deflect for insertion into the head 154. The locating steps 160 on the neck member 152 engage at least one of the grooves (e.g. the first groove 174 or the second groove 176) and one of the step faces (e.g. faces 184, 186) to engage the neck member 152 in place at a selected length relative to the first end 168 and second end 170 of the head member 154.

A person skilled in the art would appreciate that methods of engaging, besides sliding, such as rolling or clicking may be used. The user may stop pushing the neck member 152 when the locating step face 184 of the neck member 152 engages the step face 184, 186 of the selected groove, thereby arriving at the selected neck length. The user then positions the head member 154 in the patient's acetabular cup (similar to that illustrated in FIG. 6). One skilled in the art should appreciate that the click configuration is suitable outside of a patient's acetabular cup, such as during external trialing or in a shoulder.

Next, the user determines if the engaged configuration is appropriate for the patient, for example, whether the range of motion is appropriate and/or consistent with a selected patient plan. If the position is incorrect, the user may then adjust the depth of the neck member 152 within the head member 154 by removing the neck member 152 from the previously selected groove to a different groove, such as by pushing the head 154 further onto the neck 152 to engage a different groove. One or more of the markings 166, 167 may be viewed to determine that a proper change in length has been achieved by the movements. It is understood that one or both of the head member 154 and the neck member may remain in position within the acetabulum of the patient while the user adjusts the head member 154 relative to the neck member 152, or vice versa.

A Cam Adjustable Tibial Tray

Figure 11:
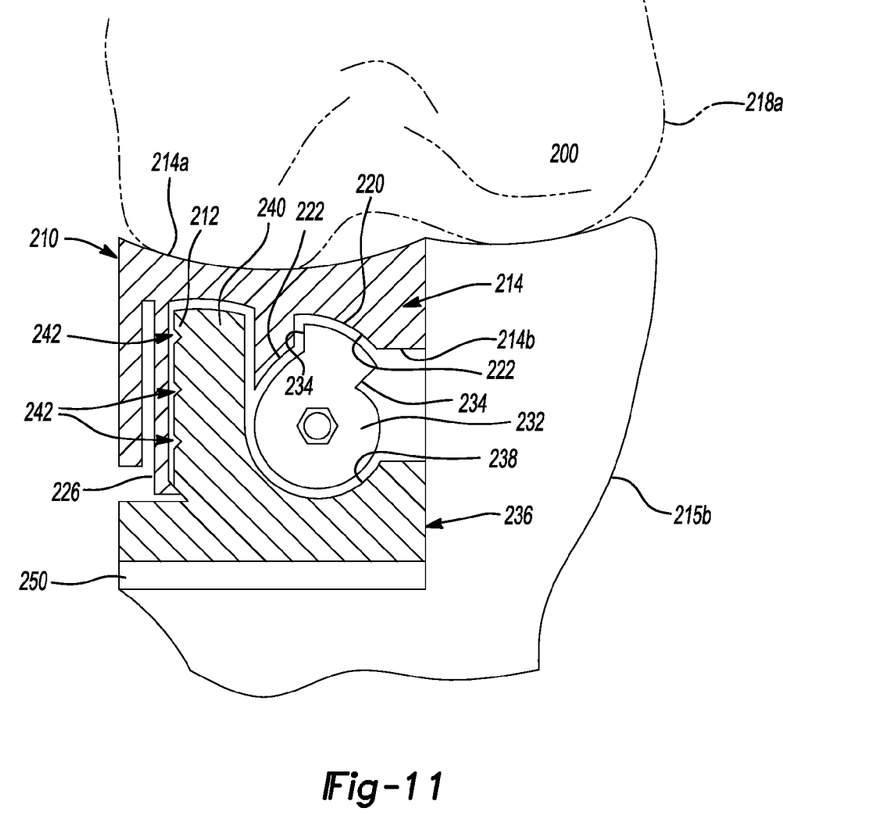
FIG. 11 is a side view of an adjustable tibial tray.

An adjustable tibial trial tray system 200 is disclosed, as illustrated in FIG. 11. A modular trial system to select a stem length, neck length, bearing thickness, tray height, or other appropriate selectable dimension is disclosed as the adjustable trial tray system 200. The adjustable trial tray system 200 includes a depth setting member 210 and an extension member 212. An adjustable trial tray system 200 includes an articulation plate 214, a cam bearing surface 220, a cam 232, and a bottom plate 236.

The articulation plate 214 may have a first side 214a and a second side 214b. The first side 214a may be provided or formed for articulation with a patient's body, such as a distal femur condyle 215a, in a manner, for example using commonly known methods and systems, such as those in the Vanguard®, Complete Knee Replacement system, sold by Biomet, Inc. The bottom plate 236 can be secured to a proximal tibia 215b or placed on a tibial tray, such as in the vanguard system. It is understood that the trial system 200 can be used with a complete knee system and/or a unicondylar knee system. The bearing portions would be augmented in size depending upon the type of knee.

The second side 214b of the surface of the articulation plate 214 has the cam bearing surface 220. The cam bearing surface 220 may be a concave surface adapted to fit the cam 232. The cam bearing surface 220 may also be made of several bearing surfaces 222 at various positions on the second side of the articulation plate 214b. The intersections of two bearing surfaces 222 create a cam stop 224.

The articulation plate 214 may also include an elongated thickness clicker 226. The elongated clicker 226 includes a neck 228 and a foot 230. The articulation plate 214 may also include a guard 233 adjacent to the elongated clicker 226 and opposite the bearing surface 220.

The cam 232 is located adjacent the cam bearing surface 220 of the second side 214b of the articulation plate 214. The cam 232 is engaged between and/or with the articulation plate 214 and bottom plate 236. The cam 232 may have multiple stop sides 234. The cam 232 is rotated from an anterior side of the prosthesis, but it could be accessed from the lateral, posterior, or medial sides. The multiple stop sides 234 interfere with the cam bearing surface 220 when the cam 232 is rotated to a stop position, as discussed below.

The bottom plate 236 may fit into a tibial tray 250 that may be secure, in an appropriate manner, to the proximal tibia 215b opposite the articulation plate 214. The bottom plate 236 includes a cam bearing surface 238 configured to fit the cam 232 with a cam stop 234. The bottom plate 236 also has an elongated thickness stop 240, which may have a plurality of stopping points 242 along its length. The stopping points 242 may be shaped as indentations distributed equidistant on the elongated thickness stop.

The thickness of the elongated thickness stop 240 is generally related to the number of stopping points 242. Therefore, having more stopping points 242 may increase the thickness of the adjustable tibial tray system 200. Each stopping point 242 corresponds to a depth setting, as discussed below. A person having ordinary skill in the art would understand that more stopping points 242 would allow more different depth settings. A thin bearing adjustable tibial tray 200 may only be able to support a few stopping points 242, therefore only a few depth settings. A user may use more than one adjustable tibial tray 200 with a different number of stopping points 242, therefore, a different thickness.

Operation of the Cam Tibial Tray

A user operates the adjustable tibial tray 200 by rotating the cam 232. In rotating the cam 232, it rotates to impart a force on the articulation 214 and bottom plates 236. Rotating the cam 232, because of the cam's 232 cammed shape, in a first direction A will impart a force to displace the articulation plate 214 and bottom plate 236 away from each other. Rotating the cam 232 in a second direction B, generally opposite the direction A, the camming force will be removed allowing a displacement of the articulation plate 214 and bottom plate 236 toward each other.

Rotating the cam 232 also causes the elongated thickness clicker 228 of the articulation plate 214 to selectively engage the elongated thickness stop 242 of the bottom plate 236. As the cam 232 displaces the articulation plate 214 and bottom plate 236, the elongated thickness clicker 228 may engage with a stopping point 242 and making a click sound to indicate engagement.

A Rotating Plate and Peg Embodiment

Figure 12A:
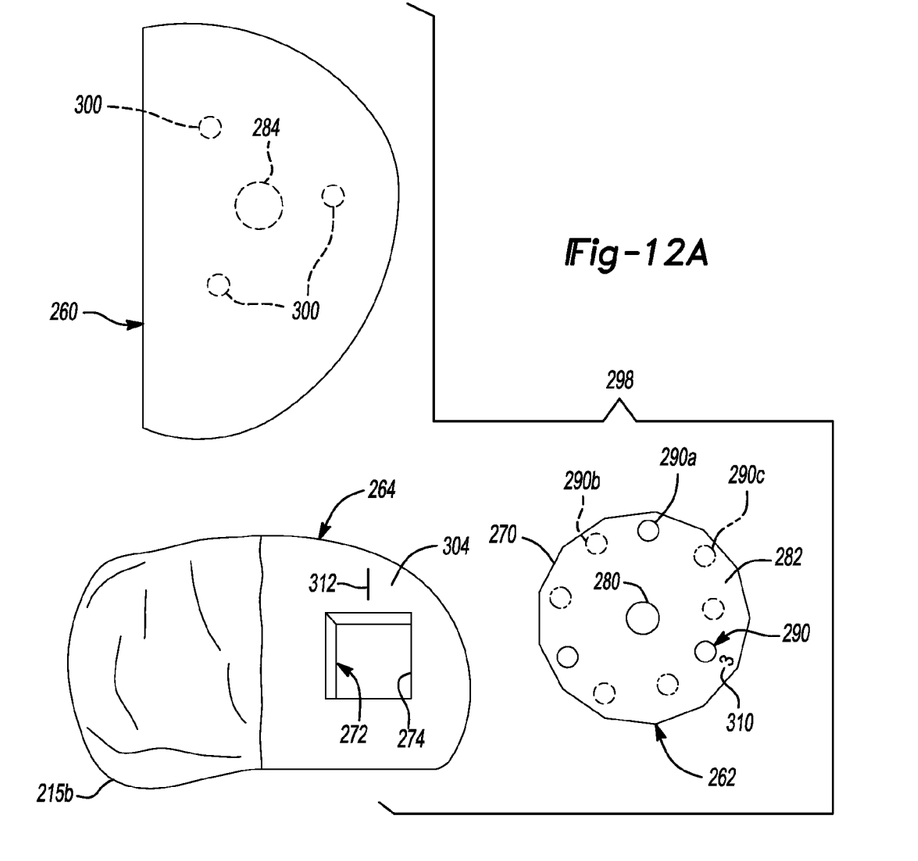
FIG. 12A is a top plan view of an assembly for a peg and plate configuration for an adjustable tray.
Figure 12B:
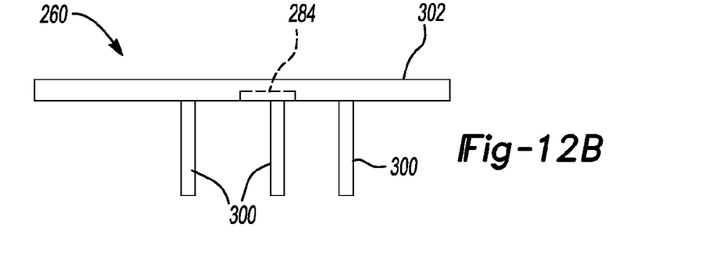
FIG. 12B is a side plan view of a peg and plate for an adjustable tray.

With reference to FIGS. 12A and 12B, a peg and plate adjustable tray embodiment 298 is illustrated. In the peg and plate adjustable tray embodiment 298 is a trialing system that can be positioned relative to the tibia 215b. In various embodiments, the trial system 298 can include a first member or bearing portion 260, a middle or second adjustment portion 262, and a third or bottom tibial surface or plate 264. It is understood that the bottom or third tibial plate 264 can be a tibial tray of a prosthetic implant or separate from a prosthetic implant, such as an Oxford® or Vanguard XP® Unicondylar tibial prosthesis, sold by Biomet, Inc. Accordingly, the trial system 298 can include, for example, the three members 260, 262, 264 or can include a tibial tray that can replace the third member 264. According to the trial system, however, an adjustable height of the first bearing member 260 can be made relative to the third member 264, which is generally fixed relative to the tibia 215b.

According to various embodiments, the middle or second member 262, can include a geometric shape including a plurality of flat sides 270. Opposed flat sides can engage a wall 272 of a depression 274 formed in the third member 264. The depression 274 can be square and include four walls or can be any other appropriate shape. The second member 262, which can also be referred to as an adjustment member 262, can be positioned within the depression 274 at various configurations relative to the third member 264 and/or the first member 260. It is understood that the adjustment member 262 can be rotated and set again into the depression 274 in the different orientations.

The adjustment member 262 can include an alignment portion, such as an alignment peg 280 which can be round and/or cylindrical such as to extend from a surface 282 of the adjustment member 262. The alignment peg 280 can engage an alignment bore or depression 284 in the top member 260. It is understood, however, that the reverse may be provided such that the adjustment member 262 includes a depression that a peg extending from the first member 260 engages. Accordingly, the alignment peg 280 can include a shape that allows it to be rotated within or to be positioned at a plurality, such as an infinite number, of positions relative to the depression 284.

Further, the adjustment member 262 can include a plurality of depressions or holes 290. The holes 290 can be provided in sets, three sets 290a, 290b, and 290c as multiples of three and be formed as depressions into the surface 282 of the adjustment member 262. Each of the sets of the depressions 290a, 290b, 290c in the adjustment member 262 can be formed at various depths or have a bottom wall at selected various and discrete depths relative to the top surface 282. According to various embodiments, four sets of the holes are provided. Each set can have a different bottom floor distance from the top surface 282. The top member or first member 260 can include pegs, such as three adjustment pegs 300 to engage all or a selected number of one set of the holes 290.

Accordingly, as the adjustment member 262 is rotated to different orientations relative to the third member 264 and set in the depression 274, different sets of the holes 290 will be aligned with the pegs 300. As each of the sets of the depressions or holes 290 have different bottom depths relative to the top surface 282, the distance of an articulation surface or bearing surface 302 of the first member 260 will be varied relative to a top surface 304 of the third member 264. Accordingly, the height or distance of the articulation surface 302 can be varied relative to the top surface 304 of the third member 264 to provide for an adjustment of the height or distance of the articulation surface 302 relative to the top surface 304 of the third member 264.

Operation of the Peg Tibial Trial Embodiment

In use, the user can position the third member 264 relative to the tibia 215b, as illustrated in FIG. 12A. As discussed above, the third member 264 can be positioned on a tibial tray or positioned against a selected portion of the tibia 215b. For example, as illustrated in FIG. 12A, the third member 264 can be part of a uni-condylar trial system such that the third member 264 can be positioned on a resected surface of the tibia 215b.

The user can position the adjustment member 262 at a first selected orientation relative to the third member 264. The user can identify a selected height by aligning the adjustment member 262 having a marking 310, such as a "3" (it is understood that the marking may be any marking, such as "10) relative to a respective indicator or marking 312 on the third member 264. By aligning the marking 310 on the adjustment member with the marking 312 on the third member 264, the user can read the selected trialed height. Accordingly, the "3" can refer to a 3 mm height (similarly a "10" may refer to a 10 mm height) of the articulation surface 302 relative to the bone surface and final implant thickness.

The user can then position the first member 260 over the adjustment member 262 and position the adjustment pegs 300 into the appropriate set of depressions 290 in the adjustment member 262. As illustrated in FIG. 12A, the first member 260 can have a selected orientation or alignment relative to the third member 264 based upon a geometry of the first member 262 and/or an anatomy of the tibia 215b. Accordingly, positioning the first member 260 in the required orientation, such as an anatomical orientation, will align the pegs 300 with one selected single set of the depressions 290 of the adjustment member 262 when the adjustment member is positioned within the depression 274.

The user can then perform a trial range of motion of the tibia 215b relative to the femur 215a (not illustrated in FIG. 12A) to determine whether a range of motion is proper. Further, a user can perform a soft tissue tension test, according to a test process as understood by one skilled in the art, to determine whether appropriate tension is provided in the soft tissue. Based upon the results of the trial, the user can then remove the top member 260 and adjust the adjustment member 262 by rotating it relative to the third member 264 to perform a further trial range of motion. After rotating the adjustment member 262 relative to the marking 312 on the third member 264, or other appropriate portion of the third member 264, the first member 260 can be re-engaged to the adjustment member 262 and a further range of motion can be trialed. Accordingly, the user can adjust the distance of the bearing surface 302 relative to the third member 264 by rotating the adjustment member 262 and fixing it within the depression 274 (such as with a friction fit) for a trial process, such as a trial range of motion. Based on the selected height, the user can then select a final implant, a bearing thickness, or other appropriate portion to achieve the identified height.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. A modular trial system to select a prosthesis length, comprising:
   a first member including at least a locating step with a locating step face formed by a surface extending at a first angle to a central axis of the first member; and
   a second member including an internal bore with a first end and a second end, wherein a first groove and a second groove are formed in the internal bore, wherein a first step face of a first step extends at a second angle relative to the central axis nearer the second end than a second step face of a second step that extends at a third angle relative to the central axis;
   wherein the locating step face is configured to selectively engage the first step face or the second step face to adjust a combined length of the first and second member; wherein the second member is selectively and discretely rotatable relative to the first member.

2. The system of claim 1, wherein the first member includes a locking feature configured to frictionally engage the second member.

3. The system of claim 1, wherein the first member has a hexagonal shape.

4. The system of claim 3, wherein the locating step is a projection extending from a wall surface of the first member, wherein the wall surface of the first member includes a plurality of wall surfaces that define the hexagonal shape of the first member.

5. The system of claim 1, wherein the first groove is parallel to the second groove.

6. The system of claim 5, wherein the first groove and the second groove are parallel to a longitudinal axis of the internal bore.

7. The system of claim 1, wherein the first member has a plurality of the locating steps and a plurality of the locating step faces, wherein each of the locating steps has one of the locating step faces.

8. The system of claim 7, wherein the plurality of locating steps are substantially evenly spaced around the neck member.

9. The system of claim 1, wherein the first member is a neck member and the second member is a femoral head.

10. The system of claim 9, wherein the neck member fits over an implant neck taper.

11. A modular trial system, comprising:
a first member including at least a locating step with a locating step face formed by a surface extending from the first member; and
a second member including a first end, a second end, a first groove defining a first step face, and a second groove defining a second step face, wherein the first step face is positioned nearer the second end than the second step face; wherein one of the first and second members is configured to be rotated such that the locating step face selectively engages the first step face or the second step face to adjust a combined length of the first and second member.

12. The system of claim 11, wherein:
the second member defines an internal bore;
the first and second grooves are formed in the internal bore; and
the locating step extends from an exterior surface of the first member.

13. The system of claim 11, wherein:
the first member defines an internal bore;
the locating step extends into the internal bore; and
the first and second grooves are formed on an exterior surface of the second member.

14. The system of claim 11, wherein the first member comprises a head member and the second member comprises a neck member.

15. The system of claim 11, wherein the first member comprises a neck member and the second member comprises a head member.

16. The system of claim 11, wherein at least one of the first and second members includes a locking feature configured to frictionally engage the other of the first and second members.

17. A modular trial system to select a prosthesis length, comprising:
a first member including an internal bore and at least a locating step with a locating step face formed by a surface extending from the internal bore at a first angle to a central axis of the first member; and
a second member including a first end and a second end, wherein a first groove and a second groove are formed in an outer surface of the second member, wherein a first step face of a first step extends at a second angle relative to the central axis nearer the second end than a second step face of a second step that extends at a third angle relative to the central axis;
wherein the locating step face is configured to selectively engage the first step face or the second step face to adjust a combined length of the first and second member; wherein at least one of the first and second members is configured to be rotated relative to the other of the first and second members.

18. The system of claim 17, wherein the first member includes a locking feature configured to frictionally engage the second member.

19. The system of claim 17, wherein the first groove and the second groove are parallel to a longitudinal axis of the internal bore.

20. The system of claim 17, wherein the first member includes a plurality of the locating steps and a plurality of the locating step faces, wherein each of the locating steps defines one of the locating step faces.

* * * * *